United States Patent
Gantes

(10) Patent No.: US 9,901,416 B2
(45) Date of Patent: Feb. 27, 2018

(54) ASSISTED DENTAL IMPLANT TREATMENT

(75) Inventor: Bernard Gantes, Long Beach, CA (US)

(73) Assignee: Cyber-Implants, LLC, Huntington Beach, CA (US)

(*) Notice: Subject to any disclaimer, the term of this patent is extended or adjusted under 35 U.S.C. 154(b) by 0 days.

(21) Appl. No.: 13/168,285

(22) Filed: Jun. 24, 2011

(65) Prior Publication Data

US 2011/0256508 A1    Oct. 20, 2011

Related U.S. Application Data

(62) Division of application No. 12/245,697, filed on Oct. 3, 2008.

(60) Provisional application No. 60/977,368, filed on Oct. 3, 2007.

(51) Int. Cl.
   *A61C 9/00*       (2006.01)
   *A61C 1/08*       (2006.01)

(52) U.S. Cl.
   CPC .............. *A61C 1/084* (2013.01); *A61C 9/004* (2013.01)

(58) Field of Classification Search
   CPC ....... A61C 8/001; A61C 8/0089; A61C 1/084; A61C 19/04; A61C 8/009
   USPC ............. 433/68, 72, 75, 172, 173, 214, 215; 700/98
   See application file for complete search history.

(56) References Cited

U.S. PATENT DOCUMENTS

| | | | |
|---|---|---|---|
| 5,236,432 A | 8/1993 | Matsen, III et al. | |
| 5,320,529 A * | 6/1994 | Pompa | 433/76 |
| 5,343,391 A | 8/1994 | Mushabac | |
| 5,725,376 A * | 3/1998 | Poirier | A61C 1/084 433/172 |
| 5,967,777 A | 10/1999 | Klein et al. | |
| 6,283,753 B1 | 9/2001 | Willoughby | |
| 6,319,006 B1 | 11/2001 | Scherer et al. | |
| 6,382,975 B1 | 5/2002 | Poirier | |
| 6,634,883 B2 | 10/2003 | Ranalli | |
| 6,788,986 B1 | 9/2004 | Traber et al. | |
| 6,793,491 B2 | 9/2004 | Klein et al. | |
| 6,966,722 B1 | 11/2005 | Malin et al. | |
| 7,168,950 B2 * | 1/2007 | Cinader, Jr. | A61C 7/146 433/2 |
| 2005/0089822 A1 | 4/2005 | Geng | |

(Continued)

*Primary Examiner* — Ralph Lewis
(74) *Attorney, Agent, or Firm* — Rutan & Tucker LLP; Hani Z. Sayed

(57) ABSTRACT

Embodiments of systems and methods for planning and/or delivering an oral or facial endosseous implantation in a patient are described. In certain embodiments, systems according to the invention include a processing module; a bone imaging module that communicates bone data about the patient to the processing module; a surface imaging module that communicates surface data about the patient to the processing module; and the processing module processes the bone data and the surface data into an output that includes three-dimensional (3-D) representation data indicative of at least one of an oral structure and a facial structure of the patient. In certain embodiments, a system includes a fabrication module that produces a physical model based on the 3-D representation data and indicating a planned location of an endosseous implant. In certain embodiments, a system includes a surgical module that guides implantation of an endosseous implant based on the 3-D representation data.

18 Claims, 11 Drawing Sheets

(56) References Cited

U.S. PATENT DOCUMENTS

| | | |
|---|---|---|
| 2005/0214716 A1 | 9/2005 | Weber et al. |
| 2006/0093988 A1 | 5/2006 | Swaelens et al. |
| 2006/0127848 A1 | 6/2006 | Sogo et al. |
| 2007/0092854 A1* | 4/2007 | Powell et al. ................ 433/213 |

* cited by examiner

FIG. 10A
OCCLUSAL VIEW:
FIG. 10B
SECTION VIEWS:
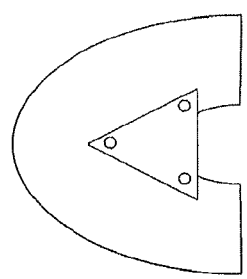
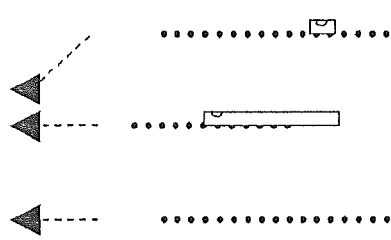
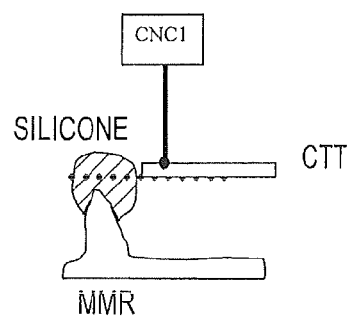
FIG. 10C

ASSISTED DENTAL IMPLANT TREATMENT

RELATED APPLICATIONS

This application is a divisional application claiming benefit under 35 U.S.C. 120 to U.S. patent application Ser. No. 12/245,697, filed on Oct. 3, 2008, which claims priority to U.S. Provisional Application 60/977,368, filed Oct. 3, 2007, the contents of which are hereby incorporated by reference herein in its entirety.

FIELD OF THE INVENTION

Embodiments of the invention relate to systems and methods for use in the production and/or delivery of dental prostheses.

BACKGROUND OF THE INVENTION

The practice of replacing missing teeth with man-made prosthetics dates to at least as early 700 BC, when the Etruscans made dentures from human or animal teeth. The first truly artificial teeth, made using porcelain, were first devised around 1770, and a British Patent for artificial teeth was granted in 1791 to De Chemant.

Since then, improvements in the design and manufacture of dental prosthetics have included the use of new materials, such as synthetic polymers and carbon fiber materials, as well as new methods of treatment planning More recently, prosthetics have advanced from the traditional surface mounted denture, to the use of permanently mounted implants surgically inserted into the underlying jaw bone, and onto which an artificial tooth or set of teeth can be mounted. These implants provide a number of advantages, including improved stability, better fit, and greater comfort.

Along with the development of improved prosthetics have been advances in the planning and delivery of replacement teeth. For example, recent methods of treatment planning include the use of imaging data to produce a virtual treatment plan, for example, Simplant® computer software as referred to in U.S. Patent Application Publication No. 2007/0059665 (Orentlicher et al.).

Virtual treatment planning systems are typically used to direct the fabrication of a surgical guide. For example, in the NobelGuide™ system, treatment planning software outputs are sent to a remote facility where a surgical guide is constructed by sterolithography techniques. The completed surgical guide is mounted in the patient's mouth and used by the dental surgeon to guide a surgical drill in order to form holes into which the implants are placed.

SUMMARY OF THE INVENTION

The use of prior art methods and devices for planning, manufacturing, and delivering dental prosthesis comes with certain limitations. For example, traditional dentures are often ill-fitting or uncomfortable for extended wear in many users. Slipping of the denture when chewing certain foods can also be problematic for patients with this kind of dental replacement.

While this problem has been partially overcome by the use of newer implant-based prosthetic systems, current implant technologies provide a less than optimal solution. For example, the present commercially available methods of applying treatment plans developed using medical imaging and software programs, to actual surgical procedures, involves the use of an intermediate surgical guide. Typically these surgical guides are fashioned by sterolithography, at a remote location, then packaged and sent to the dental professional for use in an implant procedure.

While it is possible to fashion surgical guides having acceptable fidelity with respect to the patient's oral surfaces and the virtual treatment plan, the use of these guides presents other problems. For example, the resins compatible for use in sterolithography processes are generally sensitive to moisture and ultraviolet light, as well as extremes of temperature. One manufacturer of guides warns not to allow the guide to be in contact with moisture for a period in excess of 30 minutes. The resins used for sterolithography are also generally not stable at temperatures commonly used for heat sterilization.

Production of guides by sterolithography is also relatively slow. Thus, using currently available methods and materials, an extended period of time is required to go from a first visit, the treatment planning, ordering of the surgical guide, and finally the surgical procedure and delivery of the prosthesis. This increases the cost, and reduces the attractiveness of dental implants as a prosthetic solution.

What would be desirable is a system that coordinates treatment planning, manufacture of the prosthesis, and the surgery and delivery of the prosthesis in such a way that the entire process could be accomplished within a relatively brief time period, for example within the course of a single day.

Accordingly, there is provided in some embodiments, a system, for planning an oral or facial endosseous implantation in a patient, comprising a processing module; a bone imaging module that communicates bone data to the processing module, the bone data representative of at least a portion of a bone of the skull of the patient; a surface imaging module that communicates surface data to the processing module, the surface data representative of at least a portion of a surface, of the patient, that is apart from the bone; wherein the processing module processes the bone data and the surface data into an output comprising three-dimensional (3-D) representation data indicative of at least one of an oral structure and a facial structure of the patient; a fabrication module that, based on the 3-D representation data, produces a physical model of the at least one of the patient's oral structure or facial structure, the model indicating a planned location of an endosseous implant.

In certain embodiments, a hole in the model indicates the planned location of the endosseous implant.

In certain embodiments, a surgical module, based on the 3-D representation data, guides implantation of the endosseous implant in the patient.

In certain embodiments, the bone comprises at least one of the mandible and the maxilla of the patient, and wherein the surface comprises an oral surface.

In certain embodiments, the oral surface comprises a surface of at least one of a gingiva, a tooth, and a dental prosthetic.

In certain embodiments, the system comprises a treatment planning module that, based on a combination of the 3-D representation data and input received from a treatment planner, outputs a treatment plan to a machine-readable medium, the treatment plan comprising a parameter for a planned hole in the portion of the bone; wherein the planned hole is configured to receive the endosseous implant; and wherein the parameter comprises at least one of a spatial location, a depth, a diameter, and an angular orientation of the planned hole.

In certain embodiments, the treatment planning module determines, based on at least one of a measured density, a measured absorption, and a measured intensity of a region of the portion of the bone, at least one of a number of planned holes and the parameter.

In certain embodiments, the fabrication module uses the input received from the treatment planner to produce the physical model. In certain embodiments, the system further comprises a guide module that produces a surgical guide based on the physical model. In certain embodiments, the system further comprises the physical model. In certain embodiments, the system further comprises the surgical guide.

In certain embodiments, the surface data are derived from imaging of a cast of oral structures of the patient. In certain embodiments, the imaging of the oral structures comprises imaging with at least one of computed tomography, x-ray, magnetic resonance imaging, optical imaging, acoustic imaging, and optical coherence tomography. In certain embodiments, the surface data are derived from imaging of oral structures of the patient. In certain embodiments, the imaging of the oral structures comprises imaging with at least one of computed tomography, x-ray, magnetic resonance imaging, optical imaging, acoustic imaging, and optical coherence tomography. In certain embodiments, the bone data are derived from imaging by at least one of computed tomography, x-ray, magnetic resonance imaging. In certain embodiments, one imaging device comprises both the bone imaging module and the surface imaging module.

In certain embodiments, the fabrication module comprises a milling machine that produces the physical model. In certain embodiments, the fabrication module comprises a milling machine that produces the physical model.

In certain embodiments, the treatment planner comprises a human user. In certain embodiments, the treatment planner comprises a computer program. In certain embodiments, the system further comprises the computer program.

Some embodiments of the present invention provide a system, for planning an oral or facial endosseous implantation in a patient, comprising: a processing module; a bone imaging module that communicates bone data to the processing module, the bone data representative of at least a portion of a bone of the skull of the patient; a surface imaging module that communicates surface data to the processing module, the surface data representative of at least a portion of a surface, of the patient, that is apart from the bone; wherein the processing module processes the bone data and the surface data into an output comprising 3-D representation data indicative of at least one of an oral structure and a facial structure of the patient; a surgical module that, based on the 3-D representation data, guides implantation of an endosseous implant in the patient.

In some embodiments, the bone comprises at least one of the mandible and the maxilla of the patient, and wherein the surface comprises an oral surface. In some embodiments, the oral surface comprises a surface of at least one of a gingiva, a tooth, and a dental prosthetic.

In some embodiments, the system further comprises a treatment planning module that, based on a combination of the 3-D representation and data input received from a treatment planner, outputs a treatment plan to a machine readable medium, the treatment plan comprising a parameter for a planned hole in the portion of the bone; wherein the planned hole is configured to receive the endosseous implant; and wherein the parameter comprises at least one of a spatial location, a depth, a diameter, and an angular orientation of the planned hole.

In some embodiments, the treatment planning module determines, based on at least one of a measured density, a measured absorption, and a measured intensity of a region of the portion of the bone, at least one of a number of planned holes and the parameter.

In some embodiments, the surgical module comprises a robot that, based on the treatment plan, implants the endosseous implant in the patient. In some embodiments, the surgical module comprises a robot that, based on the treatment plan, implants the endosseous implant in the patient. In some embodiments, the robot couples a dental prosthesis to the endosseous implant.

In some embodiments, the surface data are derived from imaging of a cast of oral structures of the patient. In some embodiments, the imaging of the oral structures comprises imaging with at least one of computed tomography, x-ray, magnetic resonance imaging, optical imaging, acoustic imaging, and optical coherence tomography. In some embodiments, the surface data are derived from imaging of oral structures of the patient. In some embodiments, the imaging of the oral structures comprises imaging with at least one of computed tomography, x-ray, magnetic resonance imaging, optical imaging, acoustic imaging, and optical coherence tomography. In some embodiments, the bone data are derived from imaging by at least one of computed tomography, x-ray, magnetic resonance imaging. In some embodiments, one imaging device comprises both the bone imaging module and the surface imaging module. In some embodiments, the bone imaging module, the surface imaging module, or both the bone imaging module and the surface imaging module can comprise hardware, software, or a combination thereof.

In some embodiments, the treatment planner comprises a human user. In some embodiments, the treatment planner comprises a computer program. In some embodiments, the system further comprises the computer program.

Certain embodiments of the present invention provide methods, of planning an oral or facial endosseous implantation in a patient, comprising: providing a processing module; communicating bone data to the processing module, the bone data representative of at least a portion of the bone of the skull of the patient; communicating surface data to the processing module, the surface data representative of at least a portion of a surface, of the patient, that is apart from, and near, the bone; with the processing module, processing the bone data and the surface data into an output comprising 3-D representation data indicative of at least one of an oral structure and a facial structure of the patient; with a fabrication module and based on the 3-D representation data, producing a physical model of the at least one of the patient's oral structure or facial structure, the model indicative of a planned location of an endosseous implant.

In certain embodiments, a method further comprises, with a surgical module and based on the 3-D representation data, guiding implantation of the endosseous implant in the patient.

In certain embodiments, the bone comprises at least one of the mandible and the maxilla of the patient, and the surface comprises an oral surface.

In certain embodiments, a method of further comprises, with a treatment planning module and based on a combination of 3-D representation data and an input received from a treatment planner, outputting a treatment plan to a machine readable medium, the treatment plan comprising a parameter for a planned hole in the portion of the bone; wherein the planned hole is configured to receive the endosseous implant; and wherein the parameter comprises at least one of a spatial location, a depth, a diameter, and an angular orientation of the planned hole.

In certain embodiments, the fabrication module comprises a multi-axis milling machine that produces the physical model of the patient's oral structures. In certain embodiments, the fabrication module comprises a multi-axis milling machine that produces the physical model of the patient's oral structures. In certain embodiments, a method further comprises directing, with the fabrication module and based on the physical model, a multi-axis milling machine to produce a surgical guide. In certain embodiments, a method further comprises performing, based on the surgical guide, an osteotomy.

In certain embodiments, a method further comprises installing, at the site of the osteotomy, the endosseous implant. In certain embodiments, a method further comprises installing a dental prosthesis on the dental implant. In certain embodiments, the surface data are derived from imaging of a cast of oral structures of the patient.

In certain embodiments, the imaging of the oral structures comprises imaging with at least one of computed tomography, x-ray, magnetic resonance imaging, optical imaging, acoustic imaging, and optical coherence tomography. In certain embodiments, the surface data are derived from imaging of oral structures of the patient. In certain embodiments, the imaging of the oral structures comprises imaging with at least one of computed tomography, x-ray, magnetic resonance imaging, optical imaging, acoustic imaging, and optical coherence tomography. In certain embodiments, the bone data are derived from imaging by at least one of computed tomography, x-ray, magnetic resonance imaging. In certain embodiments, one imaging device comprises both the bone imaging module and the surface imaging module.

In certain embodiments, the treatment planner comprises a human user. In certain embodiments, the treatment planner comprises a computer program.

Some embodiments provide a method, of planning an oral or facial endosseous implantation in a patient, comprising: providing a processing module; communicating bone data to the processing module, the bone data representative of at least a portion of the bone of the skull of the patient; communicating surface data to the processing module, the surface data representative of at least a portion of a surface, of the patient, that is apart from, and near, the bone; with the processing module, processing the bone data and the surface data into an output comprising 3-D representation data indicative of at least one of an oral structure and a facial structure of the patient; with a surgical module and based on the 3-D representation data, guiding implantation of an endosseous implant in the patient.

In some embodiments, the bone comprises at least one of the mandible and the maxilla of the patient, and wherein the surface comprises an oral surface. In some embodiments, the oral surface comprises a surface of at least one of a gingiva, a tooth, and a dental prosthetic.

In some embodiments, a method comprises, with a treatment planning module and based on a combination of 3-D representation data and an input received from a treatment planner, outputting a treatment plan to a machine readable medium, the treatment plan comprising a parameter for a planned hole in the portion of the bone; wherein the planned hole is configured to receive the endosseous implant; and wherein the parameter comprises at least one of a spatial location, a depth, a diameter, and an angular orientation of the planned hole.

In some embodiments, the treatment planning module determines, based on at least one of a measured density, a measured absorption, and a measured intensity of a region of the portion of the bone, at least one of a number of planned holes and the parameter.

In some embodiments, a method comprises performing, based on the treatment plan, an osteotomy.

In some embodiments, the surgical module comprises a robot that, based on the treatment plan, implants the endosseous implant in the patient. In some embodiments, the surgical module comprises a robot that installs a dental prosthesis on the endosseous implant.

In some embodiments, the surface data are derived from imaging of a cast of oral structures of the patient. In some embodiments, the imaging of the oral structures comprises imaging with at least one of computed tomography, x-ray, magnetic resonance imaging, optical imaging, acoustic imaging, and optical coherence tomography. In some embodiments, the surface data are derived from imaging of oral structures of the patient. In some embodiments, the imaging of the oral structures comprises imaging with at least one of computed tomography, x-ray, magnetic resonance imaging, optical imaging, acoustic imaging, and optical coherence tomography. In some embodiments, the bone data are derived from imaging by at least one of computed tomography, x-ray, magnetic resonance imaging. In some embodiments, one imaging device comprises both the bone imaging module and the surface imaging module In some embodiments, the treatment planner comprises a human user. In some embodiments, the treatment planner comprises a computer program.

Certain embodiments provide a system, for planning and delivering oral and facial endosseous implants in a patient, comprising: a bone imaging module that receives input data representative of at least a portion of a bone of a patient wherein the bone comprises at least one of a mandible, a maxilla and a skull of the patient; an oral surface imaging module that receives input data representative of at least a portion of an oral surface overlying a portion of the bone of the patient; a processing module that, based on data received from the bone imaging module and the oral or facial surface imaging module, outputs three-dimensional (3-D) representation data, which is indicative of a three-dimensional representation of at least one of an oral and facial structure of the patient; wherein the 3-D representation data is configured to enable production of a three-dimensional model of the oral and facial structure of the patient.

In some embodiments, the system further comprises a treatment planning module that combines the 3-D representation data, with inputs received from a treatment planner, and outputs a treatment plan comprising at least one of a spatial location, a depth, a diameter, and an angular orientation of a hole configured to receive an endosseous implant.

In some embodiments, the oral surface overlying a portion of the bone of the patient include at least one of gingiva, teeth, a dental prosthetic, and combinations thereof.

In some embodiments, the system further comprises a fabrication module that receives data inputs from the treatment planning module and produces a physical model comprising at least one of a patient's oral or facial structure, and the location of the endosseous implant. In some embodiments, the system further comprises the physical model. In some embodiments, the physical model is used as a template to manufacture a surgical guide. In some embodiments, the system further comprises the surgical guide.

In some embodiments, the fabrication module comprises a milling machine that produces the physical model of the oral or facial structure of the patient, and forms a hole in the physical model at the location of the planned implant, as determined by the treatment planning module.

In some embodiments, the inputs from the treatment planner are determined by a human user. In some embodiments, the inputs from the treatment planner are determined by a software program.

In some embodiments, the treatment planner further comprises an assistant module configured to assist in deciding the number, size, and location of the implants, based on a measurement of Hounsfield units in a region of bone that includes an implantation site. In some embodiments, the system further comprises the software program. In some embodiments, the system further comprises the assistant module.

In some embodiments, there is provided a system for planning and delivering dental implants in a patient, comprising: a bone imaging module that receives input data representative of at least a portion of a bone of a patient; wherein the bone comprises at least one of a mandible, a maxilla and a portion of the skull of the patient; an oral surface imaging module that receives input data representative of at least a portion of an oral surface overlying at least a portion of the bone of the patient; a processing module that, based on data received from the bone imaging module and the oral or facial surface imaging module, outputs 3-D representation data, which is indicative of a three-dimensional representation of an oral structure of the patient; wherein the 3-D representation data is configured to direct a surgical robot to an implantation site adapted to receive an endosseous implant.

In some embodiments, the system further comprises a treatment planning module that combines the 3-D representation data with inputs from a treatment planner and that outputs a treatment plan comprising at least one of an osteotomy spatial location, depth, diameter, and angular orientation. In some embodiments, the treatment plan is configured to direct the surgical robot to prepare the implantation site and install an endosseous implant. In some embodiments, the treatment plan is further configured to direct the surgical robot to install a dental prosthesis on the endosseous implant.

In some embodiments, the system further comprises an assistant module, configured to assist in deciding the number, size, and location of the implants, based on a measurement of Hounsfield units in a region of bone that includes an implantation site.

In some embodiments, the oral surface overlying a portion of the bone of the patient include at least one of gingiva, teeth, a dental prosthetic, and combinations thereof.

In some embodiments, the inputs from the treatment planner are determined by a human user. In some embodiments, the inputs from the treatment planner are determined by a computer program. In some embodiments, the system further comprises the program. In some embodiments, the system further comprises the surgical robot.

In some embodiments, there is provided a method, of planning and delivering dental implants in a patient, comprising: providing a bone imaging module that receives input data representative of at least a portion of a bone of a patient; wherein the bone comprises at least one of a mandible, a maxilla and a portion of the skull of the patient; providing an oral surface imaging module that receives input data representative of at least a portion of an oral surface overlying at least a portion of the bone of the patient; providing a processing module that, based on data received from the bone imaging module and the oral or facial surface imaging module, outputs 3-D representation data, which is indicative of a three-dimensional representation of an oral structure of the patient; and wherein the 3-D representation data is configured to enable an automated implantation of an endosseous dental implant to the patient's oral structure; providing a treatment planning module that combines the 3-D representation data, with an input received from a treatment planner, and outputs a treatment plan comprising at least one of a spatial location, a depth, a diameter, and a angular orientation of a hole configured to receive an endosseous implant; directing a multi-axis milling machine to produce a physical model of the patient's oral structures, based on the treatment plan; producing a surgical guide, based on the physical model; performing an osteotomy, based on the surgical guide; installing a dental implant at the site of the osteotomy; and installing a dental prosthesis on the dental implant.

Some embodiments provide a method, of planning and delivering dental implants in a patient, comprising: providing a bone imaging module that receives input data representative of at least a portion of a bone of a patient; wherein the bone comprises at least one of a mandible, a maxilla and a portion of the skull of the patient; providing an oral surface imaging module that receives input data representative of at least a portion of an oral surface overlying at least a portion of the bone of the patient; providing a processing module that, based on data received from the bone imaging module and the oral or facial surface imaging module, outputs 3-D representation data, which is indicative of a three-dimensional representation of an oral structure of the patient; and wherein the 3-D representation data is configured to enable an automated implantation of an endosseous dental implant to the patient's oral structure; providing a treatment planning module that combines the 3-D representation data, with an input received from a treatment planner, and outputs a treatment plan comprising at least one of a spatial location, a depth, a diameter, and a angular orientation of a hole configured to receive an endosseous implant; directing a surgical robot to perform an osteotomy, based on the treatment plan; installing a dental implant at the site of the osteotomy; and installing a dental prosthesis on the dental implant.

In some embodiments, the surgical robot installs the dental implant. In some embodiments, the surgical robot installs the dental prosthesis.

BRIEF DESCRIPTION OF THE DRAWINGS

FIG. 10 is a view of an embodiment of a calibration transfer template (CTT); the left panel, FIG. 10A, depicts a top view of the CTT, while the right panel, FIG. 10B, depicts side, sectional views of the CTT taken at different positions across the CTT, as depicted by the arrows. The bottom panel, FIG. 10C, illustrates one example of an alignment of the CTT and the MMR.

DETAILED DESCRIPTION OF THE INVENTION

Conceptually, there are several phases involved in the design and delivery of dental prostheses. Generally speaking, the over all process can be broken into several interdependent phases that include, without limitation, evaluation of the patient, treatment planning, manufacture of the prosthesis, surgical procedures to prepare the patient's oral structures to receive the prosthesis, and finally, delivery of the prosthesis.

Figure 1:
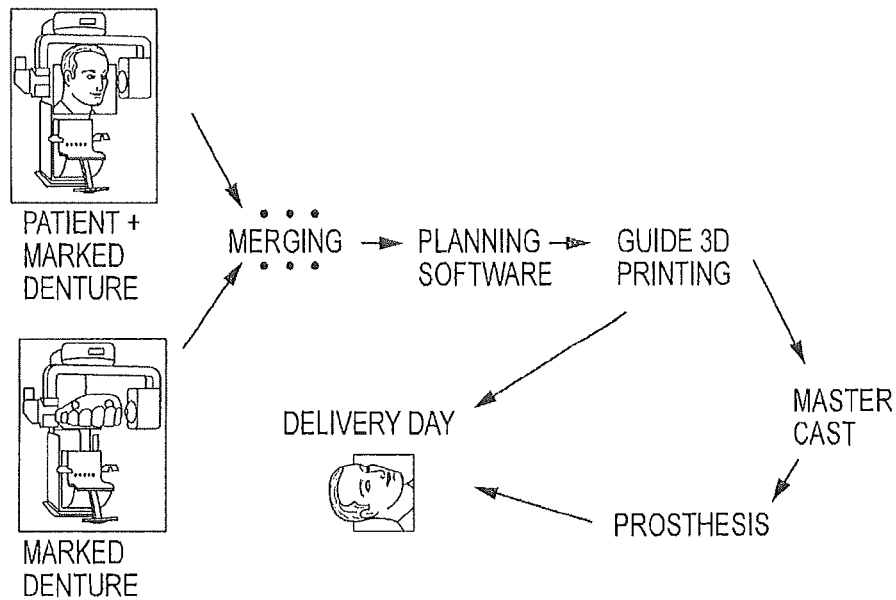
FIG. 1 is a flowchart of depicting a prior art system for planning and delivering dental implants.
Figure 2:
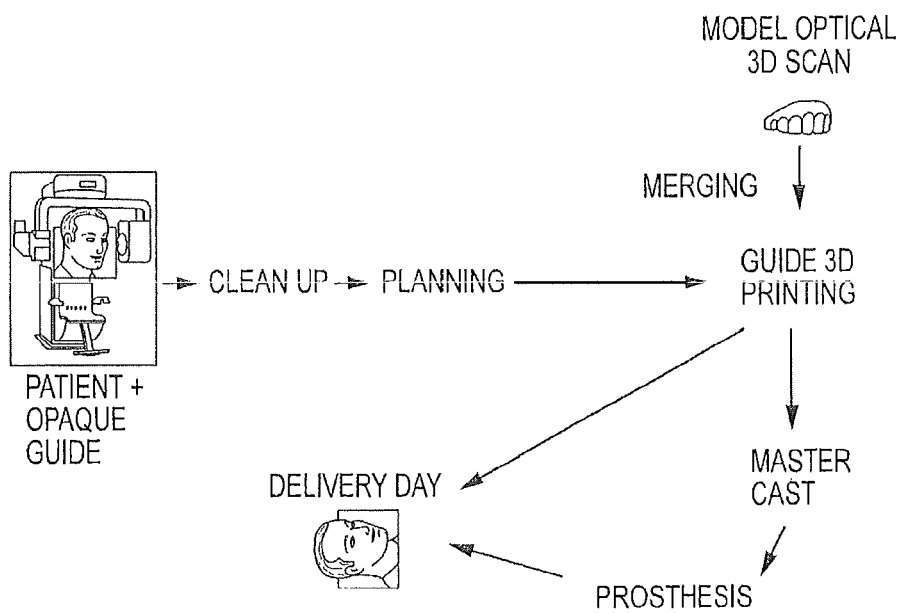
FIG. 2 is a flowchart depicting another prior art system for planning and delivering dental implants.

In certain prior art systems, such as the systems in FIG. 1 and FIG. 2, part of the initial evaluation of the patient involves CT scanning to determine the location and quality of the underlying bony components of the patient's jaw around the intended surgical site. For example, in the NobelGuide™ system, CT imagery of the patient's oral structures, and a marked denture, are merged using computer software to produce a "virtual" representation of the patient's surface oral features, in relation to the underlying hard tissue such as bone and existing teeth. If desired, existing prosthetics can be included in the CT scan as long as they are made of materials that do not generate significant scatter artifact.

This virtual representation is then imported into treatment planning software. Here, a dental professional plans the placement of osteotomy holes in the patient's gum and jaws that will receive dental implant posts. The dental prosthesis is ultimately mounted on these implant posts. The procedure can involve the placement of a single hole adapted to receive a single implant where an individual tooth is to be replaced, or multiple holes where multiple prosthetic teeth, or a row of prosthetic teeth are to be installed.

In the prior art systems, the virtual treatment plan is generally exported to an offsite facility where a surgical guide is manufactured by sterolithography. Depending on the complexity of the object to be made, sterolithography can take anywhere from a few hours to more than a day to complete. Once completed, the surgical guide is packaged and returned to the dental professional.

The surgical guide is used as a template both for the making of a master cast from which the prosthesis is derived, as well as for performing the surgical procedure. The guide includes drill guides, typically metal bushings that define the angle and depth to which an osteotomy hole will be drilled in the patient's jaw during the surgical step.

In performing the surgery, the dental professional places the guide on the patient's gum, attempts to confirm proper registration of the guide with the gum structure, and then anchors the guide in place by drilling into the jaw and then anchoring the guide with mounting screws. As the surgical guide provides the treatment plan, key to the success of the procedure is the fit of the surgical guide. Unfortunately, due a number of factors, fit can sometimes be a problem. These include problems with the CT data related to artifacts, or lack of fidelity due to data optimization between scan layers, poor fit between the soft tissues of the patient and the hard master cast, etc.

In addition, since the surgery can take place at a significant time after the original CT scan and other measurements were taken to provide the data to produce the guide, there is always a risk that on the day of surgery the guide will not fit well, due to changes in the soft tissue overlying the jaw bones. In addition, since sterolithography resin materials are generally sensitive to moisture, changes in the shape of the guide itself can occur, reducing the fidelity of fit to the patient.

Figure 3:
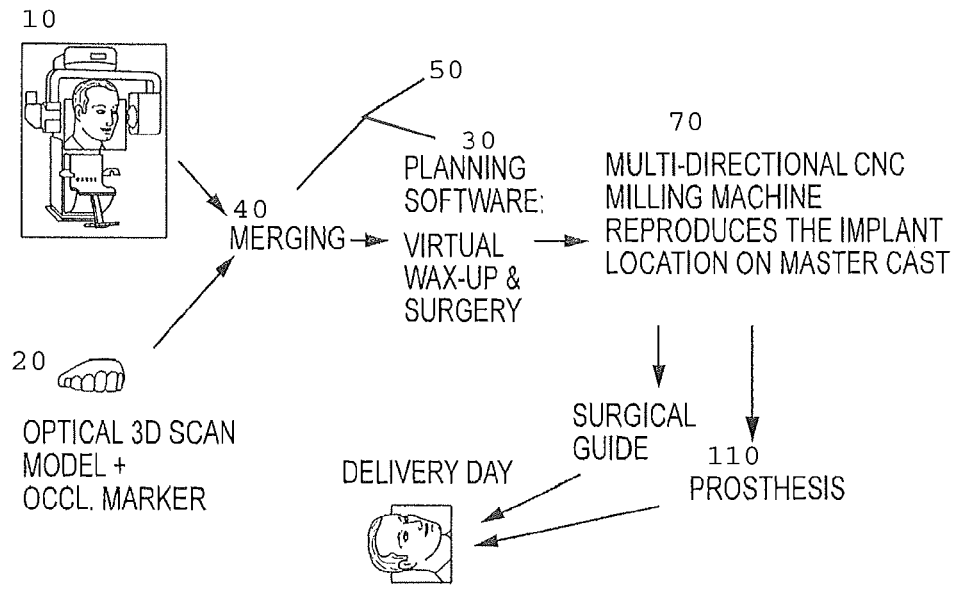
FIG. 3 is a flowchart of steps of an embodiment of a method of planning and delivering a dental prosthesis to a patient using a surgical guide produced by a multi-axis milling machine, according to the present disclosure.
Figure 4:
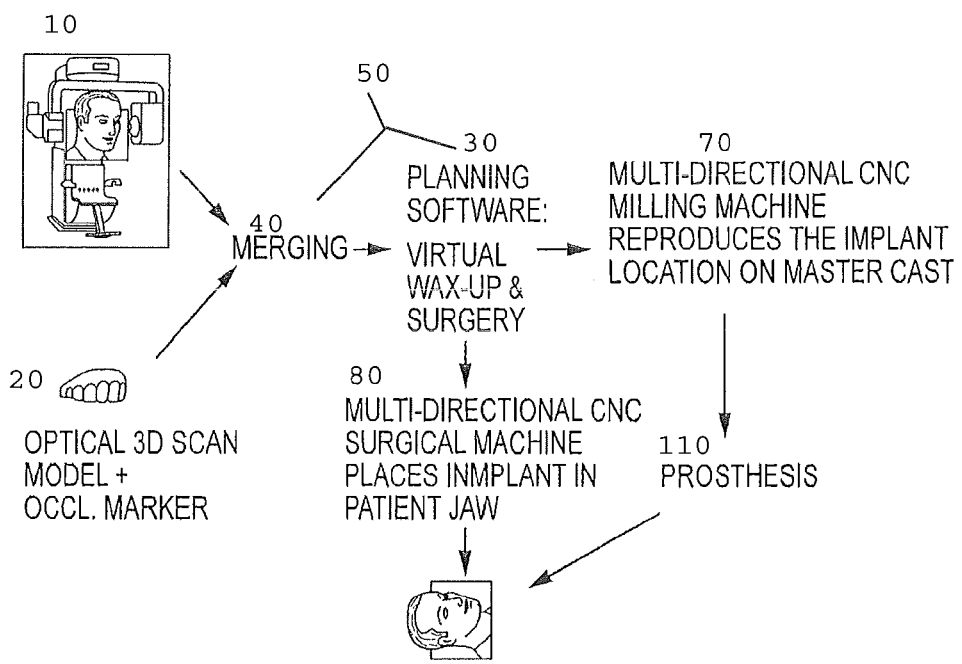
FIG. 4 is a flowchart of steps of an embodiment of a method of planning and delivering a dental prosthesis to a patient using a surgical robot, according to the present disclosure.

Therefore, embodiments of the present disclosure are directed towards a system and apparatus for use in planning treatment, performing surgery, manufacturing a dental prosthesis, and delivering the prosthesis to a patient, with high fidelity, and in a minimum time period. In particular, the described embodiments are adaptable to a system where a patient is scanned, the treatment parameters determined, and the surgery performed within a single day. FIGS. 3 and 4, provide flowchart examples of processes of planning and delivering dental implants and prostheses that improve upon the prior art. It will be understood that any of the disclosed embodiments are merely exemplary, and as such do not limit the scope of the disclosure.

Patient Imaging

As with prior art dental implant treatment systems, in the system of the present disclosure, information regarding surface and bone structures of the patient's oral and facial regions are important in implantation planning, execution of the implantation plan, and the manufacture and delivery of the finished endosseous implants and prosthesis.

Figure 5:
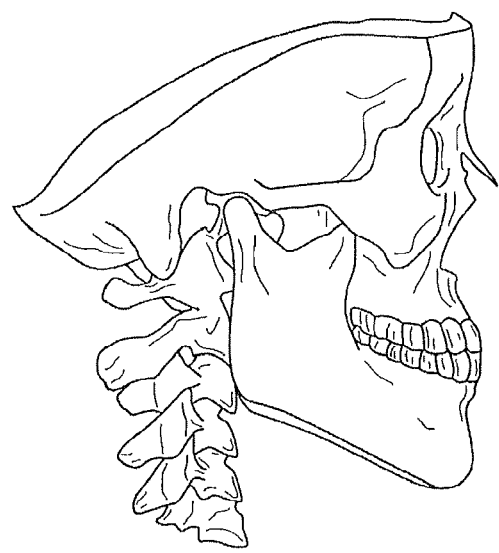
FIG. 5 is an example of a three-dimensional reconstruction of a patient's oral structures derived from computed tomography (CT) scan data.

In certain embodiments, bone structures are imaged by a bone imaging module. In some embodiments, the bone imaging module includes a CT system. In certain embodiments, imaging can be of the patient's mandible, maxilla, or both, and can include the entire bony structure of the jaw or a portion thereof. In certain embodiments, imaging can include additional bones of the skull of the patient outside the oral regions proper. An example of a CT image is provided in FIG. 5.

Various CT modalities are available that are useful in conjunction with the present system. For example, in some cases traditional spiral CT can be used. In some cases, it can be desirable to use other imaging modalities, for example and without limitation, cone beam CT. The precise type of imaging is not necessarily limiting to the embodiments of the present disclosure.

In certain embodiments, surface imaging can be achieved by optical coherence tomography ("OCT") techniques. In certain OCT techniques, an optical fiber splitter splits light from a broad band light source into optical fibers, one of the optical fibers directing light to a sample (e.g., an oral surface and a facial surface) path and another of the optical fibers directing light to a reference path mirror. A distal end of the sample path fiber can interface with a scanning device, or the like, and light reflected from the scanning device can be recombined with the signal from the reference mirror to form interference fringes that provide for precise depth-resolved imaging or optical measurements. Certain OCT techniques can measure spatially resolved backscattered intensity with a resolution on the order of a few micrometers.

Certain OCT techniques, such as Fourier domain OCT ("FD-OCT"), can achieve a high sensitivity image and a rapid imaging speed. Certain OCT techniques, such as polarization sensitive Fourier domain OCT ("PS-FD-OCT"), can reveal birefringence, diattenuation, and polarization sampling by measuring a change in polarization state. The implementation of polarization sensitivity into FD-OCT is known in the art. Certain FD-OCT systems which implement polarization sensitivity can comprise dual-channel detection paths, with two separate spectrometers, two separate line-scan cameras, or two separate lines on an area-scan camera to capture, in parallel, the spectral interferogram for two orthogonal polarization modes. Certain swept source implementations of PS-FD-OCT can employ two detection channels in a configuration similar to time-domain polarization sensitive OCT.

Certain OCT techniques can involve, e.g., a light source comprising a Ti:$Al_2O_3$ mode-locked femtosecond laser operating at, e.g., a 88-MHz pulse repetition rate, a center wavelength $\lambda o=830$ nm, and spectral bandwidth $\Delta\lambda=55$ nm Full Width Half Maximum ("FWHM"). Light that exits the source path can be collimated in open air and injected into an interferometer with an achromatic microscope objective, giving a Gaussian beam profile with a FWHM diameter of 2 mm. In certain OCT techniques, a spectrometer can be used to monitor source spectral quality, the spectrometer detects the incident spectrum as sampled. In certain OCT techniques, viewing of the incident beam location on the tissue specimen can be achieved with, e.g., visible red light $\lambda o=660$ nm), emitted by, e.g. a diode laser coupled into a multimode fiber, collimated, and combined with the source beam by a dichroic mirror. A Glan-Thompson prism polarizer can be oriented at 45° to ensure that light injected into the interferometer has equal amplitudes and zero relative phase in horizontal and vertical polarization channels. The angular orientation of all PS-OCT polarization elements can be measured clockwise with respect to the horizontal plane (x axis) viewed along the beam propagation direction (z axis); the y-axis is parallel to the Earth's gravitational field. Certain OCT techniques can be performed with continuous-wave light without the need for ultrashort laser pulses. For instance, in low-coherence reflectometry, the coherence property of light returning from an imaged sample provides information on the time-of-flight delay from reflective boundaries and backscattering sites in the sample. Optical coherence tomography's resolution is limited only by the coherence length of the optical source. Certain OCT techniques can be performed with a fibre optic Michelson interferometer illuminated by low-coherence light from, e.g., a super luminescent diode (SLD) which operates at a wavelength of 830 nm and at an optical power of 20 µW.

In certain embodiments, the light source can be a high speed scanning laser HSL-2000 with an instantaneous coherence length of over 10 mm. The swept laser source includes emitted light with a mean frequency of the output spectrum that varies over time. The mean frequency of light emitted from the swept source may change continuously over time at a tuning speed that is, e.g., greater than 100 terahertz per millisecond and repeatedly with a repetition period. A swept laser source may be any tunable laser source that rapidly tunes a narrowband source through a broad optical bandwidth. The tuning range of a swept source may have a tuning range with a center wavelength between, e.g., approximately 500 nanometers and 2000 nm, a tuning width of approximately greater than 1% of the center wavelength, and an instantaneous line width of less than approximately 10% of the tuning range. In certain embodiments, a swept laser source is coupled to an electro-optic polarization modulator to modulate the polarization state of the source light periodically in time between two semi-orthogonal polarization states.

In certain embodiments, surface imaging can be achieved by optical imaging, such as with a camera. In certain embodiments, the camera can record images on film. In certain embodiments, the camera can record images in digital format. In certain embodiments, a camera can be configured to record images with visible light, UV light, blue light, red light, infrared light, or combinations thereof. In certain embodiments, surface imaging can be achieved by acoustic imaging, such as ultrasound imaging.

In certain embodiments, surface imaging can be achieved by photoacoustic imaging, in which non-ionizing laser pulses are delivered to imaged surfaces. In certain embodiments, surface imaging can be achieved by thermoacoustic imaging in which radio frequency pulses are delivered to imaged surfaces. In certain embodiments of photoacoustic and thermoacoustic imaging, some of the delivered energy is absorbed by the imaged service and converted into heat, which means to transient thermoelastic expansion and a wideband (e.g. MHz) ultrasonic emission. The generated ultrasonic waves can be detected by ultrasonic transducers and processed to form images. In certain embodiments of photoacoustic imaging and thermoacoustic imaging, the magnitude of the ultrasonic emission, which is proportional to the local energy deposition, reveals physiologically specific optical absorption contrast from which 2-D or 3-D images of the targeted areas can then be formed.

In certain embodiments, surface imaging, bone imaging, or combinations thereof can be achieved by CT, magnetic resonance (MR) imaging, x-ray imaging, or combination thereof.

In certain embodiments, the imaging devices be configured to mount on an endoscope. In certain embodiments, the camera can be configured to be held by a human hand. In certain embodiments, the camera can be configured to mount on a stabilizing apparatus, such as a tripod.

In certain embodiments, service and bone imaging can include a step in which all pre-existing, removable metal-containing prostheses are removed from the imaged facial and/or all region of the patient prior to imaging in order to reduce the likelihood of scatter artifact. Where the patient has a small edentulism with stable natural occlusion, the scan can be performed without a removable scanning prosthesis, as the existing teeth are adequate to place the mandible and maxilla in a position representative of the patient's normal occlusion.

Where the patient has a large or complete edentulism, the scan can be performed with an all-acrylic functional removable prosthesis or with a functional acrylic replica. A functional prosthesis is defined as one where the prosthesis incorporates an accurate reproduction of the edentulous ridge mucosa (or gum), and an accurate and esthetically acceptable occlusal relation with the other arch. Thus, the acrylic replica simulates the space occupied by a normal set of teeth, and places the mandible and maxilla in a relatively normal position for the purposes of the scan. Those of skill in the art will readily appreciate that various functional replicas will be useful in practicing the methods of the present disclosure.

Prior to scanning with a functional replica, several x-ray labels (e.g., Surmark® labels) can be evenly placed on the functional replica portion contacting the mucosal ridge crest. The patient can then be scanned with the replica in place. During scanning the patient instructed to apply moderate biting force on the replica so that the oral structures remain relatively compressed. Where the patient has an unstable bite, a silicone bite block can be used during scanning to aid in maintaining a stable configuration of the oral structures.

In addition to imaging the underlying bony structures, the surface contours of at least a portion, and sometimes all, of the patient's oral structures are obtained by way of a surface imaging module. There are various methods of acquiring surface contour information, and various types of surface imaging modules that are useful in the context of the present disclosure.

In some embodiments, imaging of the surface contours of least a portion of the patient's oral structures can be performed. Various ways of accomplishing this are possible, one of which is disclosed in U.S. Pat. No. 5,343,391 (Mushabac), by laser optical surface scans (Soncul et al., J. Oral Maxilofac. Surg., 2004, 62: 1331-1140), or using a stereo multi-camera 3-D photographic structures (Otis et al., J. Am. Dent. Assoc., 131:511-514). The contents of each of these references are incorporated by reference in their entireties.

In some embodiments, the dental professional will make a casting of the patient's oral structures, and imaging of the cast can be performed to acquire information related to the patient's oral surface contours.

Regardless of the method employed, the result will be the acquisition of information related to the three-dimensional (3-D) relationship of the patient's existing teeth (if any) and gingiva. In some embodiments, the casting can include an occlusion marker to provide information regarding the relative meshing of the patient's upper and lower dentition.

Treatment Planning

Once data representing the surface contours of the patient's oral structures, as well as the underlying bony structures have been obtained, a computer software algorithm is used to merge the two datasets. The merged dataset provides a 3-D representation of both the surface and underlying structures. The merged data can then be used to provide a virtual 3-D representation of the patient's bony structures (derived from CT scanning) and surface features (from optical or other scanning methods)—i.e., a 3-D virtual patient reconstruction. The 3-D representation can conveniently be displayed on a computer screen or other visual display, and displays the gingiva, teeth, if any, and bony structures. The software will also permit manipulation of the displayed image to allow virtual rotation of the "patient" in any axis. Being able to rotate the virtual "patient" permits the dental professional to more effectively plan hole locations and trajectories by being able to assess bony structures from multiple angles. This will in turn result in the optimization of implant location and stability when implants are surgically placed in the patient's jaw.

For patients with a small edentulism, mapping can be done with the aid of the crowns of existing teeth. For patients who are largely or completely edentulous, mapping can be done with the aid of x-ray markers, which are visible on both the CT and optical scans.

Figure 6:
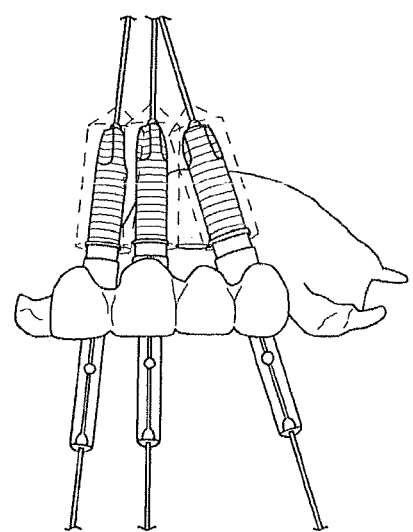
FIG. 6 is a computer display showing an example of a virtual treatment plan produced using the NobelGuide™ system.

The next step in the process involves developing the virtual treatment plan. Generally, the treatment plan will include determining the location, angle (trajectory), depth, orientation of implant head, and width, of holes to be created in the patient's jaw during the surgical phase of the process. In some embodiments, the treatment plan can be a virtual treatment plan, created using computer algorithms that permit the virtual placement of one or more "implants" in a 3-D representation of the patient's jaws and/or oral surface contours. An example of a treatment plan display is provided in FIG. 6.

In planning treatment, the dental professional is provided a number of possible virtual operation choices. For example, where a patient has a small edentulous region, the space can be virtually reconstructed by selecting an appropriately sized and shaped "tooth" from a database library. Where one or more teeth are to be extracted, the socket size can be estimated from the root shape. Thus, implants from the library can be conceptually "placed" according to the estimated existing alveolar volume and socket size following virtual extraction.

Figure 7:
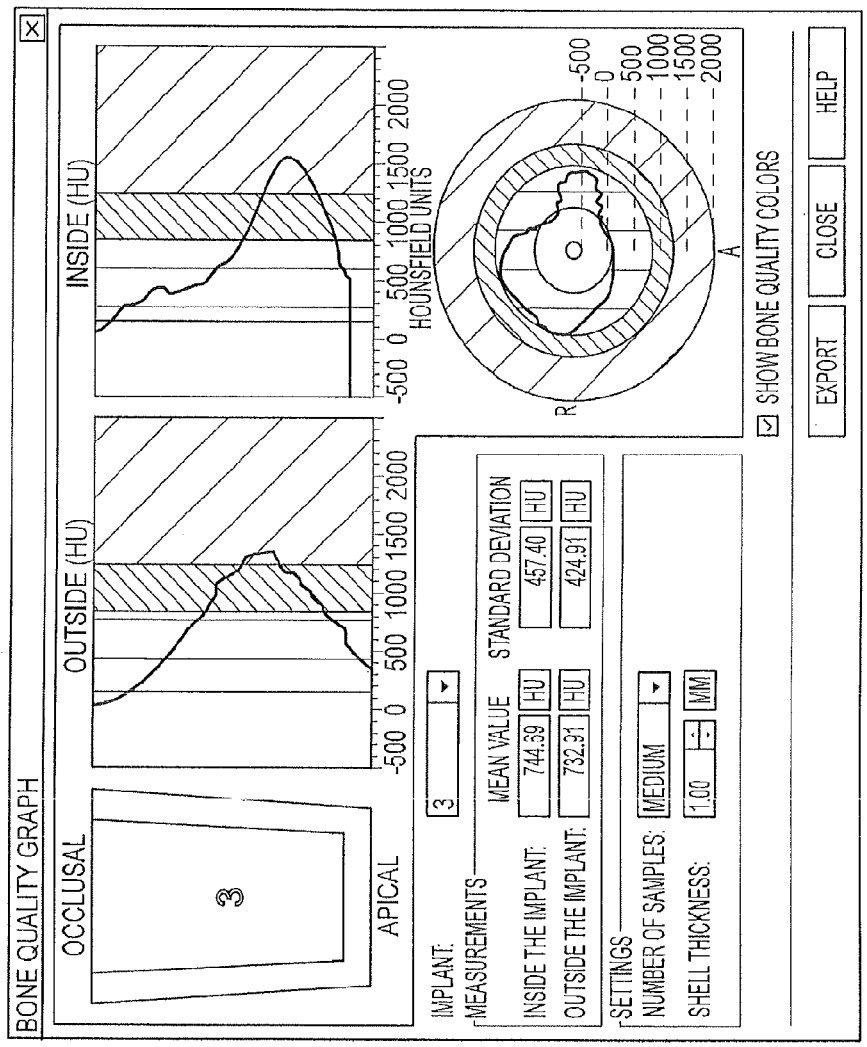
FIG. 7 is a computer display showing a bone density software tool (Simplant).

In some embodiments, the system will include an assistant module. The assistant module will generally comprise a software program that receives inputs from the CT scanner or other devices, and outputs information about bone density or other relevant structural information with relation to the intended site of implantation. The assistant module can be further programmed to automatically select a most preferential implant site, or to warn the surgeon about possible problems with nerves or other objects one would wish to avoid damaging during surgery. For example, the assistant module could provide the dental professional with an output related to bone quality that relates to bone density (e.g., Hounsfield unit map), as shown in FIG. 7. In some embodiments, a treatment planning module and an assistant module can be the same.

In some embodiments, the treatment planning module could be entirely automated, such that based on the CT scan and surface imaging data, the planning module could plan the placement of dental implants based on the same "rules" a dental professional would use in determining where best to place an implant.

In some embodiments, the treatment planning module can be used to perform a virtual extraction of a tooth, or teeth. This feature allows for simultaneous extraction, implant placement, and prosthesis delivery. None of the prior art systems provide this capability.

Machined Master Replica

It is to be understood that any and all references to the use of any machine, for example any computer-numerical controlled multi-axis milling machine (CNC), in the description that follows are merely exemplary, and are not in any way limiting to the scope of the disclosure or claims. Thus, any apparatus or device that is able to perform any steps of any method or to produce any object as described herein is intended to fall within the scope of the invention.

In some embodiments, the virtual treatment plan will be used in the production of a replica of the patient's oral structures. In some embodiments, a pre-shaped resin block can be mounted on a computer-numerical controlled multi-axis milling machine (CNC1), although any machine capable of shaping objects can be used. The block can be pre-shaped to permit reproducible placement of the resin block on the CNC1, such that a number of manipulations involving either the CNC1 or other dental laboratory procedures can be performed on the resin block while maintaining registration of the physical block with the virtual treatment plan.

After mounting the block on the CNC1, milling of the resin block can be performed to produce a milled block that replicates the patient's oral surface features. While the underlying bony or other tissue information is not milled into the block, the system nevertheless includes data corresponding to the position of underlying structures relative to the surface features, as well as data related to the treatment plan developed with the treatment planning software.

Figure 8:
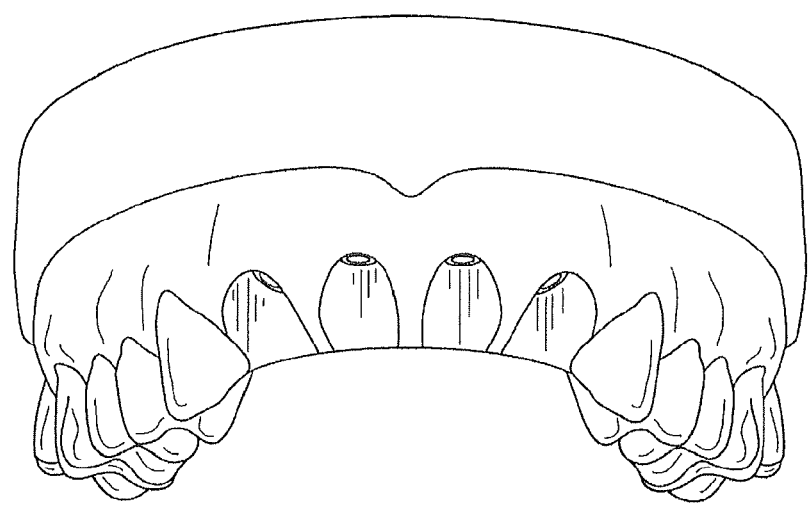
FIG. 8 is a display of a machined master model (MMR) after virtual extraction of the four incisors.

The relevant clinical data of a patient (e.g., teeth, edentulous ridges, gums, and "virtual extractions") can be reproduced on the resin block using the CNC1. Next, implant analogs (replicas of the surgical implants will be installed in the patient's jaw) can be placed into the machined resin block according to the virtual treatment plan. In some embodiments, placing of the analogs involves first drilling holes into the resin block of a diameter, depth, trajectory, and implant head orientation, based on that determined during virtual treatment planning. The placement and positioning of the analogs can be controlled by the CNC1, acting on instructions received from the treatment planning software. An example of a simulated replica with mounted analogs is provided in FIG. 8. The oral structures represented in FIG. 8 are made from a cast, but replicate what a machined replica with installed analogs would look like.

The result is a model of the patient's oral structures, with implants installed. This model is termed a machined master replica (MMR). The MMR can be placed in a semi-adaptable articulator along with a functional prosthesis acrylic replica to confirm proper occlusion.

The MMR provides several advantages over prior art methods of making oral replicas. The MMR can be made of a variety of materials that are stable and easy to work with. For example, the MMR can be made from a resin blank immediately upon completion of the treatment planning. Unlike prior art methods of casting, no time is required to wait for the casting material to harden. In addition, the use of an MMR avoids the need to wait for the availability of the 3-D printed surgical guide, which prior art methods use in the manufacture of the prosthesis.

In addition, as the virtual treatment plan includes in its database the relationship between the surface features, and the underlying bony structures into which the implants will be installed, the dental professional can use an MMR as a practice model on which to replicate the treatment plan to confirm the esthetic and functional quality of the treatment plan, prior to delivering the prosthesis to a live patient.

In some embodiments, the MMR can be used as a template with which to fashion a prosthesis. In making the prosthesis, traditional laboratory methods can be used.

Figure 9:
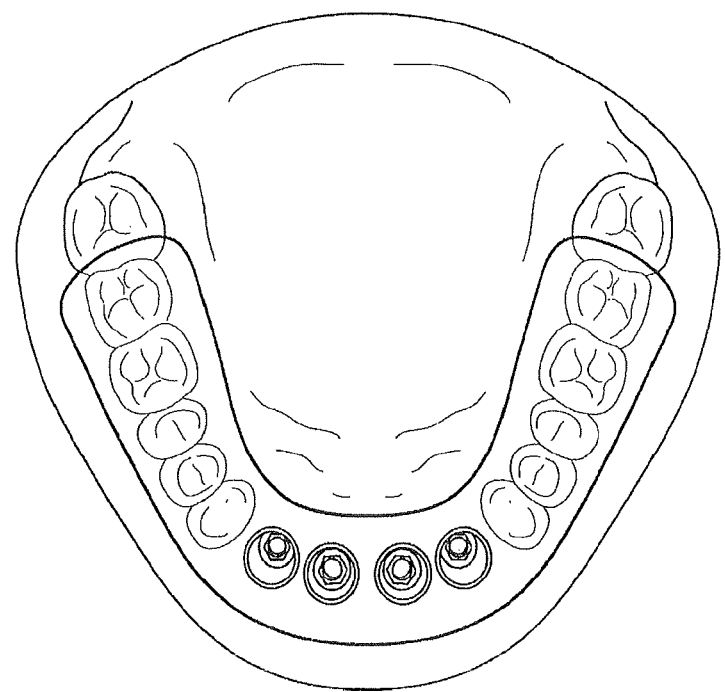
FIG. 9 is a display of the same MMR covered with a laboratory made surgical guide.

The MMR can also be used in order to fashion a surgical guide, as shown in FIG. 9. The surgical guide can be molded using the MMR as a template. Since the guide is being molded from the MMR, materials such as self-curing polymers or plastics can be used as the mold material. This will avoid problems due to the nature of materials used to make surgical guides by sterolithography. For example, in some embodiment, the surgical guide can be made from materials that are not adversely affected by moisture, or UV light, and which are chemically stable enough to permit sterilization by autoclaving, or alternatively, by chemical sterilization methods. Surgical guides can also be fashioned from metal, or heat resistant plastic as well. Further, since an MMR can be rapidly made, it is possible to produce several identical MMR replicas, thus allowing different aspects of the procedure to be performed at the same time. For example, with three MMRs, one can be used to manufacture a surgical guide, one can be used for practicing the surgery, and one could be used to manufacture the prosthesis, all of which could occur essentially simultaneously. The MMR can also be used for simulating tooth extractions.

After making a surgical guide using the MMR as a template, drill guides can be placed into the surgical guides. In some embodiments, drill guides comprise generally open tubes with a lumen of a pre-selected diameter. The drill guides can be mounted into the surgical guide, as shown in FIG. 9, where they define the location and trajectory of the hole to be placed in the patient's jaw and which receives the implant. The central hole in the drill guide is sized large enough to accommodate the desired drill bit without resulting in binding of the bit in the sleeve while the drill is operating. Binding of the drill bit in the guide can cause excessive friction which in turn leads to heat generation during the drilling process. Excessive heat can damage adjacent tissues, and so the drill guide must be sized to allow free rotation of the drill bit. Drill guides can be fashioned from a number of suitable materials, including, without limitation, surgical steel, ceramics, polymers, and the like.

In some embodiments, a treatment planner can comprise a human being. In some embodiments, a human treatment planner can provide input by, e.g., marking a planned hole parameter on a virtual or physical 3-D representation at the planned location site of an endosseous implant with, for instance, a computer marking device, e.g., a mouse or a touchscreen device or a physical marking device, e.g., a pen, a pencil, or a chisel, respectively. In some embodiments, a treatment planner can comprise a computer program. In some embodiments, a computer treatment planner can provide input by, e.g., directing the marking a planned hole parameter on a virtual or physical 3-D representation at the planned location site of an endosseous implant with, for instance, a computer marking device or a physical marking device, respectively.

Calibration Template

In some embodiments, a CTT is produced, as shown in FIG. 10. The CTT will generally be fashioned from a rigid material, and will include three or more calibration marks, which can be in the form of depressions placed at various locations on a surface of the CTT. In some cases the CTT is roughly triangular in shape and includes calibration marks arranged near each vertex of the CTT.

The CTT can be adapted to the MMR using silicone or other suitable adhering material. Once the CTT has been immobilized relative to the MMR, the combination of replica and calibration template are mounted on a CNC1 machine. The CNC1 machine is then used to record to relative position of the calibration marks in the CTT, and this data is included in the virtual treatment plan data. In some embodiments, recorded positional calibration data and the CTT are later used to calibrate a second CNC machine, for example, a CNC2 machine, which can be used in performing the surgery, as well as in the installation of the prosthesis.

Surgical Procedures

Figure 11:
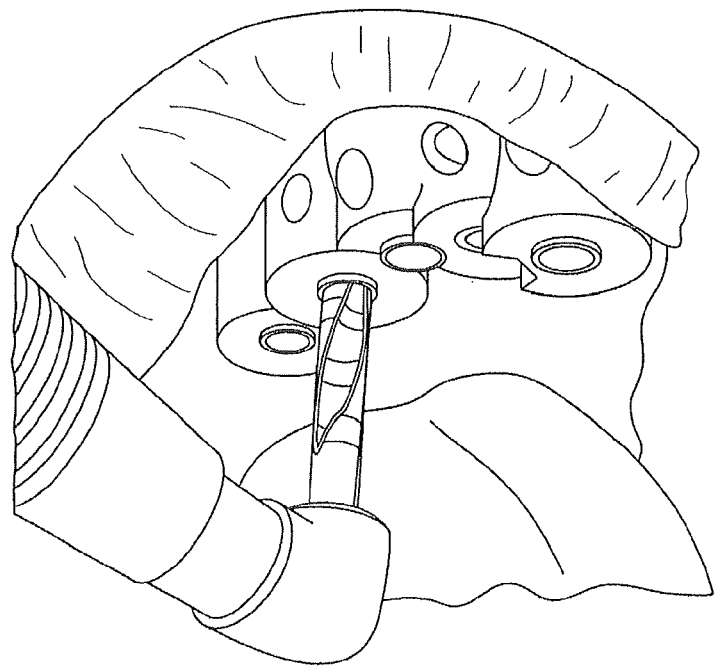
FIG. 11 is a view of a surgical guide, including drill guides, produced by the NobelGuide™ surgical system.

Prior art methods of surgical delivery of implants generally employ a common approach. A surgical guide is mounted on the patient's jaw. The surgical guide includes drill guides that direct the dental professional's hand in terms of location and trajectory of holes to be drilled into the jaw and into which implants will eventually be mounted. An example of a surgical procedure using a physical guide is shown in FIG. 11.

Figure 12:
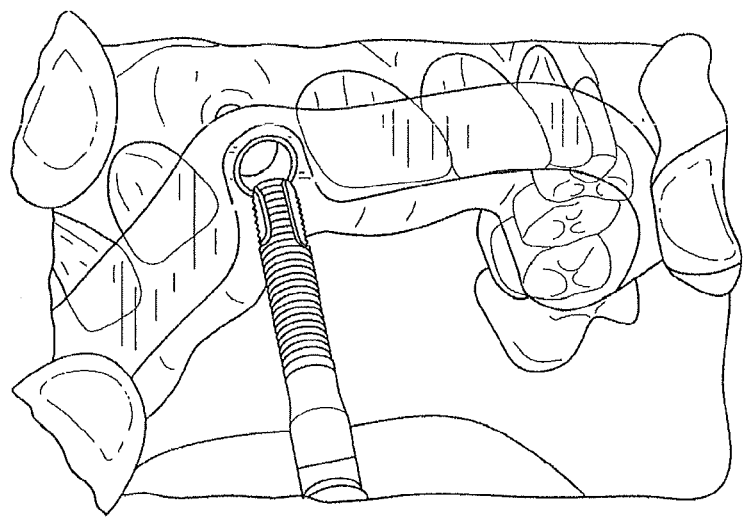
FIG. 12 is view of an extraction with simultaneous implant placement using a surgical guide fabricated from a MMR after virtual extraction, as performed using the Nobel-Guide™ surgical system.

In some embodiments of the present disclosure a surgical guide, like that shown in FIG. 9, can be produced using the MMR. The surgical guide includes one or more drill guides corresponding to desired locations for performing an osteotomy according to the treatment plan. The surgical guide can be mounted in the patient's mouth by standard procedures. Unlike prior art guide produced by sterolithography, the surgical guide of the present disclosure is produced using the MMR as a template, and can be made from materials more suitable for use in an aqueous, and preferably hygienic working environment. This provides, among other things, a better fitting surgical guide, and one that can be produced nearly immediately after completion of the treatment planning phase.

Where a surgical guide device is used, the dental professional will place the device in the patient's mouth, confirm correct alignment, then fix the surgical guide in place. The dental professional then uses an appropriate sized drill bit to form the holes in the jaw into which the implants are subsequently placed. An example of a surgical guide in place, with the osteotomy complete, and the implant in position for delivery is shown in FIG. 12. In some embodiments, a guide module and a bifurcation module can be the same device.

The surgical guide is designed to ensure that the hole drilled follows the desired path and extends to the desired depth, as determined in the treatment plan. Once the holes are drilled, the dental professional can then install the implants into the holes. In some embodiments the implant is threaded, and thus is screwed into the newly formed hole. Other shapes and configurations are also useful in conjunction with the methods described herein, and so the particular style of implant is not considered to limit the disclosure in any way. The implants themselves can be made from a variety of materials that are biocompatible, and which will encourage bone growth around the implant in order to further stabilize it.

In some embodiments, for example the method outlined in FIG. 4, a surgical guide is not used, but instead surgery is performed directly by a surgical robot, programmed with information in the treatment plan. Where "guideless" surgery is performed, treatment planning, surgery, and delivery of the prosthesis can be done in a completely virtual environment. In this case, to ensure accuracy of the process, the anatomical structures of the "live" patient, and those of the "virtual" patient can be calibrated with respect to each other.

This can be done in several ways. In one example, the CTT and MMR coupled to each other, and then probed by the CNC1 machine. The CNC1 determines the relative position of calibration marks included on the CTT, and maps the position of those marks with respect to analogous calibrations on the MMR. Note that the position of underlying (i.e., non-surface) structures have already been mapped relative to the surfaces features as represented in the MMR. Thus, the calibration process provides data that relates the surface features, the underlying structures, and the treatment plan, to produce a comprehensive dataset that allows the CTT to calibrate, for example, a CNC2 machine so that it can accurately replicate the treatment plan on the live patient.

In some embodiments, the calibration marks can be hemispherical depressions in the CTT that match the shape of a probe end on an arm of the CNC1 machine, as illustrated in FIG. 10. The precise shape size and location of calibration marks on the CTT are not limiting, nor is the precise structure of the probe mechanism on the CNC1 machine.

The CNC2 machine can be configured to move a drill bit along a trajectory with respect to the patient's oral structures, and to drill holes in the patient's jaw to a predetermined depth, based on the virtual treatment plan. Using a CNC2 surgical robot permits automated surgery without the need for a surgical guide device. In this way, any error in positioning a surgical guide in the patient's mouth can be avoided and thus the procedure can nearly perfectly reproduce the treatment plan on the patient. It will be understood that the use of a CNC2 machine as a surgical robot is merely an example, and is not limiting to the scope of the disclosure. Any surgical robot, or like device, that can perform any step or produce any product as described herein, is considered to be included within the scope of the present disclosure. Thus, in some embodiments, a single machine suitably equipped, is able to perform all the tasks as described herein. Accordingly, the use of separate CNC1 and CNC2 machine is merely exemplary and does not limit the disclosure in any way.

In performing surgery using a surgical robot it sometimes useful to provide the surgical robot, for example a CNC2 machine, with an accurate 3-D frame of reference with respect to the patient's oral structures. As discussed, one aspect of this involves the accurate calibration of the CTT with respect to the MMR and the treatment plan. In addition, the patient's head must be secured relative to the CNC2 surgical robot, such that the frames of reference between the CTT, the patient, and a CNC2 machine are maintained in registration throughout the surgery.

Figure 13:
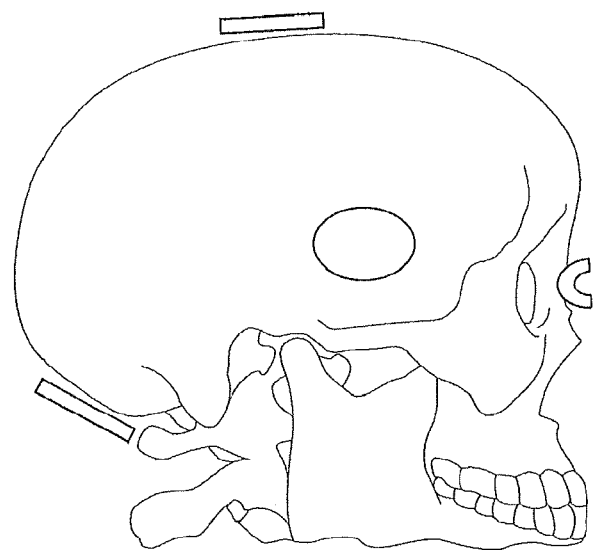
FIG. 13 is a radiographic side view of a patient's skull and/or oral structures, and one example of extra-cranial support placements (open white shapes overlying the radiograph) when performing surgery on the upper jaw.
Figure 14:
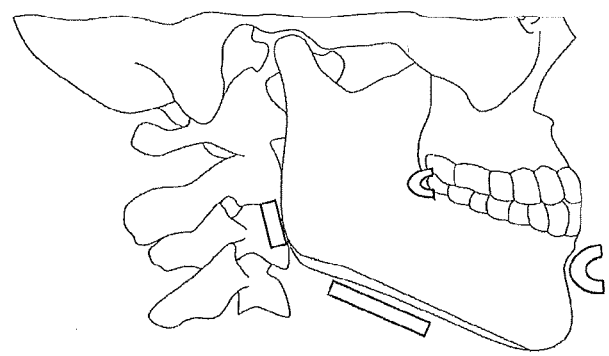
FIG. 14 is a radiographic side view of a patient's skull and/or oral structures, and one example of extra-cranial support placements (open white shapes overlying the radiograph) when performing surgery on the lower jaw.

In some embodiments, stable, externally located cranial supports are used to immobilize a CNC2 machine relative to the patient's skull and/or oral structures. As shown, supports can be used to immobilize either the upper jaw or the lower jaw. In some cases both upper jaw and lower can be immobilized.

Where surgery is to be performed on the upper jaw, it is sufficient to use a number of extra-oral supports, as the upper jaw is anatomically fixed relative to the skull, as illustrated in FIG. 13. When performing lower jaw surgery, it can be advantageous to use both extra-oral supports as well as intra-oral supports, as shown in FIG. 14.

Figure 15:
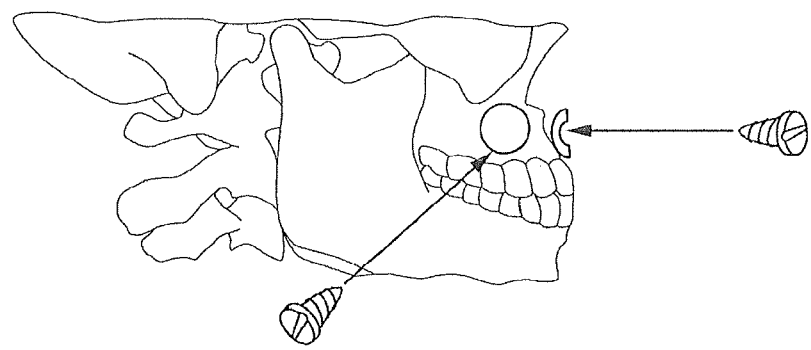
FIG. 15 is a radiographic side view of a patient's skull and/or oral structures, and an example of an intra-oral support fixated with orthopedic screws, one facial and two lateral, for use when performing surgery on the upper jaw.
Figure 16:
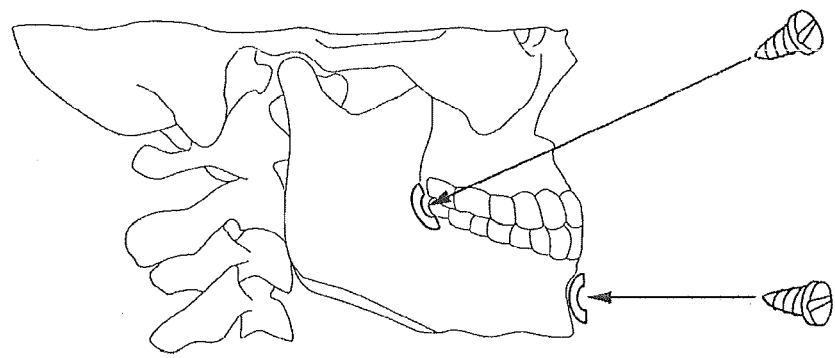
FIG. 16 is a radiographic side view of a patient's skull and/or oral structures, and an example of an intra-oral support fixated with orthopedic screws, one on the symphysis and two on oblique branches of the mandible, for use when performing surgery on the lower jaw.

The extra-cranial support system is effective to couple the 3-D frames of reference of the CNC2 surgical robot, the CTT, the treatment plan, and the patient. The connection can be released if desired, for example, if the need arises to abort the surgical procedure for safety or other reasons.

Where this external support system is not sufficiently stable, for example, due to unusual anatomical features of the patient, a modified support system can be used. In one example, the support can be fixed intra-orally by three small arms fixated to the jaw through the mucosa using orthopedic fixation screws, for example 1.5 to 3 mm diameter and 5 to 10 mm long screws, as illustrated in FIGS. 15 and 16.

Once the patient has been immobilized relative to the surgical robot, for example, a CNC2 machine, the 3-D frames of references can be aligned, such that the CNC2 machine is in registration with the location of the patient's surface features, the underlying bony structures, and the treatment plan. In one example of a method for aligning the patient and the surgical robot, the CTT is placed in the patient's mouth, and a robotic arm of the CNC2 can be used to map the location of the calibration marks on the CTT. As these calibration marks were previously mapped and recorded relative to the MMR, once the calibration of the CNC2 is complete, the CNC2 will possess an accurate relative map of the orientation of the patient's oral structures, as represented by the MMR, as well as the location of underlying structures present in the virtual patient representation (VPR), as well as the data corresponding to the treatment plan.

Calibration can include additional checks to ensure the fidelity of the alignment between the VPR and the patient's actual oral structures. In some embodiments, a check procedure can include directing the CNC2 probe to touch various pre-determined locations within the patient's mouth. In patient's with teeth, these could be specific spots on an existing tooth. Here the surgeon could easily confirm that the CNC2 was able to precisely locate specific positions, thus confirming the fidelity of the calibration procedure. In edentulous patients, other markers could be used. For example, small minimally invasive marker devices could be planted at various points along the gums, and the CNC2 could be directed to touch those points to confirm the calibration is accurate.

Once the CNC2 has been calibrated, the osteotomy can take place. Various procedures are available, including both "flap" and "flapless" surgery. When flap surgery is used, a portion of the overlying gum tissue is dissected and peeled back to give the dental professional direct access and a view of the underlying bone. When flapless surgery is used, the dental professional can, optionally, use a round tissue punch to remove soft tissue overlying the bone at the intended implant site, exposing the bone beneath. In some methods, the dental professional can drill directly through the mucosa.

Once access to the underlying bone is achieved, a surgeon can drill a hole for an implant. Holes can be drilled by the surgeon using a surgical guide made as described above. In some cases, the drilling of holes will be performed by the CNC2 surgical robot. Using the CNC2 machine obviates the need for a surgical guide device as all of the treatment plan parameters are programmed into the software that directs the CNC2 machine. Therefore, the CNC2 machine will be directed to drill holes in the patient's jaw at a pre-determined trajectory, and to a pre-determined depth. The caliber of the hole will be dictated by the drill bit used.

In some embodiments, the operator will manually change the drill bit mounted on the CNC2 drill head according to the treatment plan. In some embodiments the tool selection can also be made to be automatic, such that the CNC2 machine includes additional capabilities to change tools according to software directions included in the treatment plan data.

The CNC2 machine can include, without limitation, other features useful in the surgical procedure, such as apparatus for cleaning out the freshly drilled holes and for removing debris, blood, or saliva, or camera systems to enable remote viewing or recording of the procedure. The CNC2 can also include display capabilities that output various parameters such that the surgeon can monitor progress of the treatment plan. The CNC2 can also include an emergency interrupt system so that in case of emergency the surgery can be safely and quickly paused or terminated. The surgical robot can operate regardless of the orientation of the patient's head.

Installing the Prosthesis

Once the implant holes are completed and cleaned, the CNC2 machine can also be used to deliver the prosthesis. As the CNC2 includes in its programming the entire treatment plan, including the shape and intended placement of the prosthesis, it can be readily adapted to put the prosthesis in place, as well as complete any other functions associated with the installation. Installation of the prosthesis by the CNC2 surgical robot can include, without limitation, placing the prosthesis on the implant abutments and then fastening the prosthesis to the implant(s). In some embodiments a biostable adhesive is used to affix the prosthesis to the implant. In some embodiments, the prosthesis can be affixed by fasteners such as screws and the like. In some embodiments a prosthesis can additionally be anchored to pre-existing teeth.

Flow Chart

Figure 17:
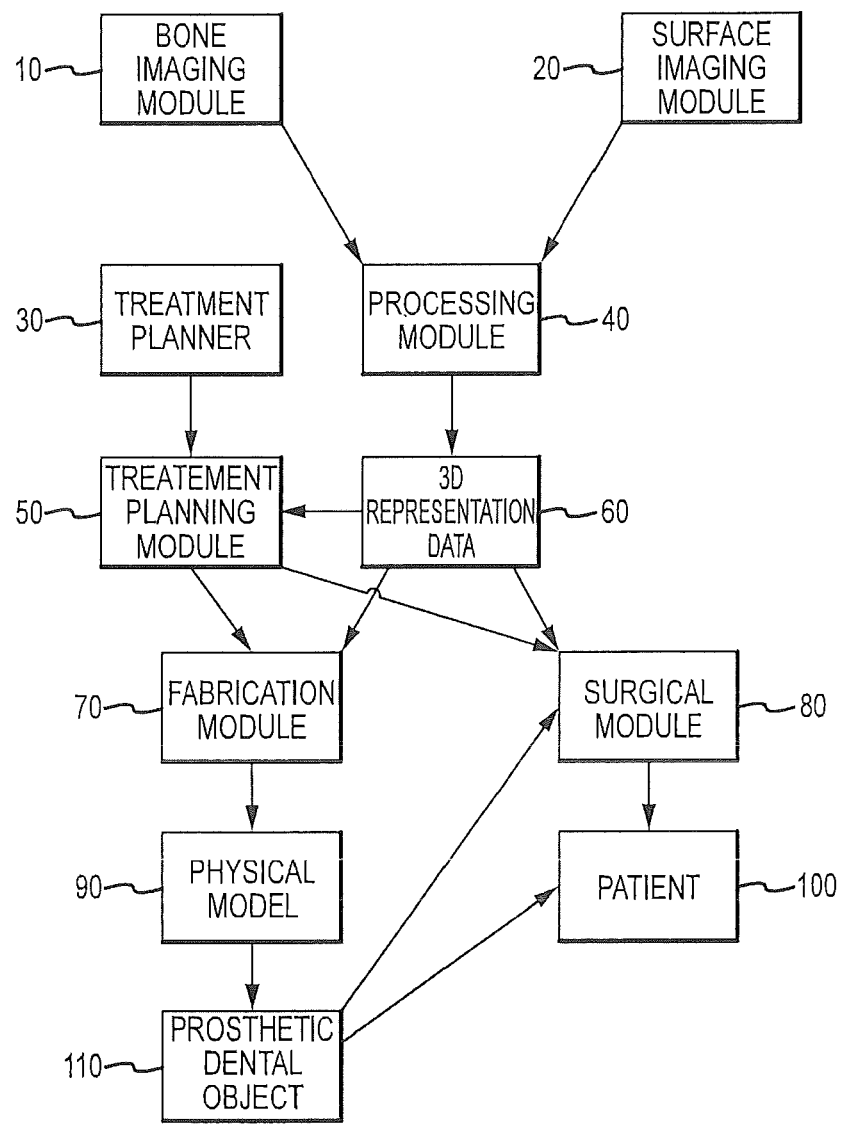
FIG. 17 illustrates certain embodiments of systems and methods of the present invention, in the form of a flow chart of exemplary modules and exemplary flows of inputs and outputs to and between them.

As illustrated in FIG. 17, certain systems of the present invention provide for planning an oral or facial endosseous implantation in a patient, and comprise a processing module 40; a bone imaging module 10 that communicates bone data to the processing module 40, the bone data representative of at least a portion of a bone of the skull of the patient; a surface imaging module 20 that communicates surface data to the processing module 40, the surface data representative of at least a portion of a surface, of the patient, that is apart from the bone. In certain embodiments, a single module can comprise both the bone imaging module and the surface imaging module. In certain embodiments, the processing module 40 processes bone data and surface data into an output comprising three-dimensional (3-D) representation data 60 indicative of at least one of an oral structure and a facial structure of the patient.

In certain embodiments, a fabrication module 70, produces, based on the 3-D representation data 60 and/or inputs from a treatment planning module 50, a physical model 90 of the at least one of the patient's oral structure or facial structure, the model indicating a planned location of an endosseous implant. In some embodiments, a treatment planning module 50 outputs, based on a combination of the 3-D representation data 60 and input received from a treatment planner, information, e.g., a treatment plan, to a machine-readable medium, the treatment plan comprising a parameter for a planned hole in the portion of the bone; wherein the planned hole is configured to receive the endosseous implant. In some embodiments, the parameter comprises at least one of a spatial location, a depth, a diameter, and an angular orientation of the planned hole. In some embodiments, a surgical module 80 guides, based on the 3-D representation data, implantation of an endosseous implant in the patient 100.

In some embodiments, the treatment planning module 50 outputs, based on a combination of the 3-D representation data 60 and data input received from a treatment planner 30, a treatment plan comprising a parameter for a planned hole in the portion of the bone, the planned hole configured to receive the endosseous implant. In some embodiments, such a parameter can comprise at least one of a spatial location, a depth, a diameter, and an angular orientation of the planned hole. In some embodiments, the treatment planner 30 can comprise a human being and/or a computer program. In some embodiments, the treatment planning module 50 can, in response to input from the treatment planner 30 and/or the 3-D representation data 60, output information, e.g., a treatment plan, to a fabrication module 70 or to surgical module 80. In certain embodiments, the fabrication module 70, based on the information from the treatment planning module 50 and/or the 3-D representation data 60, produces the physical model 90. In certain embodiments, a prosthetic dental object 110, e.g., an implant, a prosthetic tooth, or a combination thereof, can be formed, at least in part, based on the physical model 90. In certain embodiments, the surgical module, based on outputs from the treatment planning module 50 and/or the 3-D representation data 60, implants, or direct the implantation of, the prosthetic dental object 110 in the patient.

The skilled artisan will recognize the interchangeability of various features from different embodiments. Similarly, the various features and steps discussed above, as well as other known equivalents for each such feature or step, can be mixed and matched by one of ordinary skill in this art to perform compositions or methods in accordance with principles described herein. Although the disclosure has been provided in the context of certain embodiments and examples, it will be understood by those skilled in the art that the disclosure extends beyond the specifically described embodiments to other alternative embodiments and/or uses and obvious modifications and equivalents thereof. Accordingly, the disclosure is not intended to be limited by the specific disclosures of embodiments herein.

The invention claimed is:

1. A method, of planning an oral or facial endosseous implantation in a patient, comprising:
    providing a processing module;
    communicating bone data to the processing module, the bone data representative of at least a portion of the bone of the skull of the patient;
    communicating surface data to the processing module, the surface data representative of at least a portion of a surface, of the patient, that is apart from, and near, the bone;
    with the processing module, processing the bone data and the surface data into an output comprising three-dimensional (3-D) representation data indicative of at least one of the group consisting of an oral structure and a facial structure of the patient;
    with a fabricator and based on the 3-D representation data, producing a physical model of the at least one of the patient's oral structure and the facial structure of the patient, the model indicative of a planned location of an endosseous implant;
    an assistant module to generate an output being a graphical display illustrating bone data including at least one of (i) a size or a location of the endosseous implant, (ii) an implant measurement, or (iii) a Hounsfield unit map, wherein the bone data is based on a measurement of Hounsfield units in a region of the bone that includes the planned location;
    producing a calibration template from a rigid material, the calibration template including at least one calibration mark on a surface of the calibration template;
    adhering the calibration template to the physical model; and
    providing mounted analogs separate from and inserted in the physical model representing surgical implants to be installed in the patient's jaw.

2. The method of claim 1, further comprising outputting a treatment plan, based on a combination of the 3-D representation data and input received from a treatment planner, that permits virtual placement of one or more virtual implants in a 3-D presentation of the patient's jaws and/or oral surface contours displayed on a screen.

3. The method of claim 1, wherein the producing of the physical model is achieved without casting the physical model.

4. A method, of planning an oral or facial endosseous implantation in a patient, comprising:
    providing a processing module;
    communicating bone data to the processing module, the bone data representative of at least a portion of the bone of the skull of the patient;
    communicating surface data to the processing module, the surface data representative of at least a portion of a surface, of the patient, that is apart from, and near, the bone;
    with the processing module, processing the bone data and the surface data into an output comprising three-dimensional (3-D) representation data indicative of at least one of the group consisting of an oral structure and a facial structure of the patient;
    with an assistant module that receives the bone data and surface data, generating an output being a graphical display illustrating bone data including at least one of (i) a size or a location of the endosseous implant, (ii) an implant measurement, or (iii) a Hounsfield unit map, wherein the bone data is based on a measurement of Hounsfield units in a region of the bone that includes the planned location;
    with a computer implemented computerized surgical module and based on the 3-D representation data, guiding implantation of an endosseous implant in the patient.

5. The method of claim 4, wherein the bone comprises at least one of the group consisting of the mandible and the maxilla of the patient, and wherein the surface comprises an oral surface.

6. The method of claim 5, wherein the oral surface comprises a surface of at least one of the group consisting of a gingiva, a tooth, and a dental prosthetic.

7. The method of claim 4, further comprising, with a treatment planning module and based on a combination of the 3-D representation data and an input received from a treatment planner, outputting a treatment plan to a machine readable medium, the treatment plan comprising a parameter for a planned hole in the portion of the bone;
    wherein the planned hole is configured to receive the endosseous implant; and
    wherein the parameter comprises at least one of the group consisting of a spatial location, a depth, a diameter, and an angular orientation of the planned hole.

8. The method of claim 7, wherein the treatment planning module determines, based on at least one of the group consisting of a measured density, a measured absorption, and a measured intensity of a region of the portion of the bone, at least one of a number of planned holes and the parameter.

9. The method of claim 7, further comprising performing, based on the treatment plan, an osteotomy.

10. The method of claim 7, wherein the treatment planner comprises a human user.

11. The method of claim 7, wherein the treatment planner comprises a computer program.

12. The method of claim 4, wherein the surface data are derived from imaging of a cast of oral structures of the patient.

13. The method of claim 12, wherein the imaging of the oral structures comprises imaging with at least one of the group consisting of computed tomography, x-ray, magnetic resonance imaging, optical imaging, acoustic imaging, and optical coherence tomography.

14. The method of claim 4, wherein the surface data are derived from imaging of oral structures of the patient.

15. The method of claim 14, wherein the imaging of the oral structures comprises imaging with at least one of the group consisting of computed tomography, x-ray, magnetic resonance imaging, optical imaging, acoustic imaging, and optical coherence tomography.

16. The method of claim 4, wherein the bone data are derived from imaging by at least one of the group consisting of computed tomography, x-ray, and magnetic resonance imaging.

17. The method of claim 4, wherein one imaging device comprises both a bone imaging module for communicating the bone data and a surface imaging module for communicating the surface data.

18. The method of claim 4, further comprising outputting a treatment plan, based on a combination of the 3-D representation data and input received from a treatment planner, that permits virtual placement of one or more virtual implants in a 3-D presentation of the patient's jaws and/or oral surface contours displayed on a screen.

* * * * *